United States Patent [19]

Chitulescu et al.

[11] 4,006,223

[45] Feb. 1, 1977

[54] DRUG COMPOSITION INTENDED FOR THE TREATMENT OF ACUTE, LETHAL AND CHRONIC RADIATION DISEASE

[75] Inventors: Irina Chitulescu; Octav Costachel, both of Bucharest, Romania

[73] Assignee: Spitalul Clinic Filantropia Bucuresti, Bucharest, Romania

[22] Filed: Dec. 16, 1974

[21] Appl. No.: 532,861

[52] U.S. Cl. .............................. 424/177; 424/200; 424/202; 424/274

[51] Int. Cl.$^2$ ................ A61K 37/00; A61K 37/26

[58] Field of Search ...................... 424/177

[56] References Cited

UNITED STATES PATENTS

| | | | |
|---|---|---|---|
| 3,855,197 | 12/1974 | Hirsch et al. | 424/177 |
| 3,872,075 | 3/1975 | Butti et al. | 424/177 |

OTHER PUBLICATIONS

Evans et al.: Chem. Abstr. 75:115718f (1971).
Tutochkina et al.: Chem. Abstr. 72:51558g (1970).
Paulov et al.: Chem. Abstr. 72:75378z (1970).
Mandel et al.: Chem. Abstr. 66:16926e (1967).
Markova: Chem. Abstr. 73:127,493a (1970).
Kuzin et al.: Chem. Abstr. 70:64934k (1969).

*Primary Examiner*—Lewis Gotts
*Assistant Examiner*—Reginald J. Suyat
*Attorney, Agent, or Firm*—Karl F. Ross; Herbert Dubno

[57] ABSTRACT

Pharmaceutical compositions comprising an $\alpha_1$ glycoproteic complex, a lipoprotic complex, a kalikrein-inhibitor polypeptide, thiaminediphosphate and L-tryptophan are disclosed. The compositions may be administered to afflicted man and animals to treat radiation disease without prior and exact determination of the time of exposure to the radiation.

5 Claims, No Drawings

DRUG COMPOSITION INTENDED FOR THE TREATMENT OF ACUTE, LETHAL AND CHRONIC RADIATION DISEASE

The present invention relates to a new pharmaceutical composition effective in the treatment of radiation disease in man and animals.

Radiation disease starts in about twelve infraclinic, clinically non-expressed syndrones (e.g. molecular, cellular) which later develop into about ten other clinically expressed functional and lethal syndrones (e.g. organic, tissular, homeostatic, etc.). Methods are known concerning the chemical treatment of the radiation disease; different sulfur compounds: aminoethyl-lisothiuronium and mercaptonoethyl guanadine; different amines; anaesthesizing and tranquilizing drugs, polysaccharidic polymers; extracts of the anterior hypophysis; ACTH; adrenalin; testosteron; hexoestrol; corticoids; ATP; vitamins etc. have been applied.

All of the above have disadvantages: Some are not effective in sub-toxic doses while in toxic doses (for mammals) the animals are killed as a result of latent toxicity; others produce hebitude and become ineffective after two to three administrations.

The most effective of the above-mentioned drugs (of the AEt type) are effective only for an exact period (about 50 minutes) before radiation exposure in order to be present in maximum concentration in the subject's blood level at the time of irradiation. Therefore, all present chemical treatments of radiation disease are exclusively prophylactic. The treatments are completely ineffective if administered after irradiation. Also, as mentioned earlier, all prophylactic treatments mandatorily require exact knowledge of the subject's time of exposure to the radiation so that at that time the drug may be present in maximum concentration in the subject's bloodstream.

At present, the only effective treatment administered to the subject after exposure is autogenic bone marrow perfusion. The bone marrow is harvested before the irradiation, prepared, maintained at $-180°$ C, heated and reinoculated immediately or within 24 hours after irradiation.

However, autogenic bone-marrow harvesting from the entire population, the establishment of banks for conserving the marrow at $-180°$ C in sufficient amounts, and distribution of the marrow are very difficult.

Finally, the use of bone marrow to treat radiation poisoning is open to chance. The risk exists of alteration of the bone marrow cells. There is no absolutely secure procedure for conserving the cells and their maximum storage life is about 6 months at best. The duration of one bone-marrow administration lasts for about one hour and the rapid mass administration of sterile bone marrow is at present practically impossible.

The object of this invention is to provide a pharmaceutical composition, low in cost and non-toxic, that may be administered without adverse side effects to a subject that has already been exposed to radiation poisoning.

Another object is to provide a method of treatment of mammalian subjects for radiation exposure.

The invention is a pharmaceutical composition which comprises an $\alpha_1$ glycoproteic complex, a lipoproteic complex (both prepared in and available from the Oncological Institute Bucharest), a kalikrein-inhibiting polypeptide, thiaminediphosphate, and L tryptophan, which are administered as soon as possible to a subject suffering from radiation poisoning. Also, pharmaceutical compositions are disclosed which comprise L arginine in addition to the above-mentioned compounds. The invention is illustrated in the following examples:

EXAMPLE 1

White common Wistar or R inbred rats (130. ±5 g.) totally irradiated by 950 R (rads) $Co^{60}$ (which is a LD 100/30), receive immediately after irradiation for a period of from 2 to 20 days at the same time each day a pharmaceutical composition comprising 1 mg. of the lipoproteic complex, and $5 \times 10^3$ to $10^4$ KIU of the kalikrein-inhibitor polypeptide + 4 mg thiaminediphosphate, 4 mg. L tryptophan and 4 mg. L arginine which is administered by injection.

EXAMPLE 2

Adult pigs (70 kg ±3 kg) of York strain were teleirradiated with 340 rads $Co^{60}$ - (LD 80/30), and received thereafter a pharmaceutical composition comprising 30 mg of the lipoproteic complex, and $5 \times 10^4$ to $10^5$ KIU of the kalikrein-inhibitor polypeptide and 150mg thiaminediphosphate and 100 mg. of L-Tryptophan and 100 mg. of L-argenine through injection.

EXAMPLE 3

In chronic ulcerations (1 to 2 years old resulting from overexposure in radiotherapy) in man, 0.8 mg/kg body weight of thiamin disphosphate are administered each 2 to 3 days intramuscularly, intravenously or intraarterially along with 1 mg/kg body weight L tryptophan, 0.5 mg/kg body weight of the beforementioned lipoproteic complex and $10^3$ KIU/kg of body weight kalikrein-inhibiting polypeptide mentioned hereinbefore, for from 10–15 days per month for 2 to 3 months until the ulceration is completely closed.

The composition is administered daily or every 2–4 days for a period of 2–30 days; the treatment model tends to be in accord with the pharmacodynamic proprieties of the administered substances, e.g.: the half biological life (2 hours in peripheral blood) of the mentioned polypeptide, which in certain administration schedules has an antagonic action towards the thiaminediphosphate; the thiaminediphosphate associated to L arginin and/or L tryptophane, determines in the following 24 hours the cellular DNA replication and mitoses in an important percentage (2–20 × as compared to nontreated controls) in liver, thymus and spleen of common Wistar and R inbred rats.

After arriving at the maximum decrease in the peripheral blood leukocyte number (function of the dose received) the treatment is continued only by the association thiaminediphosphate/L tryptophan and L arginine, until the peripheral leukocyte restoration is obtained.

The radiation doses are counted as follows:

1. White common Wistar or R inbred rats (130 g ± 5 g) totally irradiated by 950 R $Co^{60}$ (which is a LD 100/30), receive immediately after irradiation during 2–30 days and at the same day hour the mentioned drug composition as mentioned above.

2. Adult pigs (70 kg ± 3 kg) of York strain, whole body teleirradiated with 340 rads $Co^{60}$ –(LD 80/30), receive the following 30 days after irradiation the drug composition as mentioned above.

The amount of administered substances is different for each animal species and according to the response to radiations.

The drug composition can be used for counteracting acute lethal radiation disease or chronic radiation disease after military irradiations, professional irradiations, excessive radiotherapy (e.g. ulcerations) and in cytostatic disease.

The drug composition appears to act on the indirect (abscopal) radiobiological effect, is non-toxic in efficient doses for mammals, is efficient because it is administered exclusively after irradiation, may be used by every medical doctor, auxilliary personnel, in injections in vehicles which could be easily deposited in their usable form.

The drug composition may also be carried and individually or group administered.

The invention has the advantage that an optimal efficiency is obtained with the drug composition by applying it starting with the first hour after irradiation, eliminating the necessity of a previous knowledge of the instant of irradiation. The drug composition proposed is not toxic and has no secondary or adverse effects on the treated subjects. The substances comprised in the drug composition are stable and can be kept (up to 3 years) in large scale or individual storage at the room temperature. The drug composition does not appear to have species or strain specificity and acts especially on the hemorrhagic syndrome, which are most serious in pig and man. The drug composition can be carried and administered individually to every subject casually irradiated by himself or by a neighbour immediately after irradiation. The duration of administration lasts for about 5 min. The cost of the drug composition is low, it is about 10% of the treatment by congelated bone marrow (180° C), which has a similar efficiency.

What is claimed is:

1. A pharmaceutical composition which comprises from 1 to 30 mg of a lipoproteic complex, $5 \times 10^3$ KIU of a kalikrein inhibiting polypeptide, from 4 to 150 mg. of thiaminediphosphate and from 4 to 100mg of L tryptophan.

2. The composition of claim 1 which further comprises from 4 to 130 mg of arginine.

3. A method of treating radiation poisoning in mammals comprises injecting the afflicted subject after irradiation with a pharmaceutical composition which comprises from 1 to 30 mg of a lipoproteic complex, from $5 \times 10^3 - 5 \times 10^5$ KIU of a kalikrein inhibiting polypeptide, from 4 to 150 mg. of thiaminediphosphate and from 4 to 100 mg of L tryptophan.

4. The method of claim 3 wherein the pharmaceutical composition further comprises from 4 to 100 mg of arginine.

5. A pharmaceutical composition for the treatment of the acute lethal, or chronic radiation disease and its adverse effect in mammals, consisting of for one daily dose: $1 \times 10^3$ to $8 \times 10^5$ KIU of a kalikrein inhibitor polypeptide, 1 mg to $2 \times 10^2$ mg thiaminediphosphate, 0.1 mg to $10^2$ mg of $\alpha_1$ glycoproteic complex; 1 mg to $2 \times 10^2$ mg L tryptophane, 1 mg to $10^3$ mg L-arginine and 0.1 mg to $10^2$ mg of a lipoproteic complex.

* * * * *